United States Patent
Little et al.

(10) Patent No.: US 8,018,687 B1
(45) Date of Patent: Sep. 13, 2011

(54) DISK DRIVE WITH FLEX CABLE BRACKET HAVING ALIGNMENT POST BY FLEX EXIT LOCATION

(75) Inventors: Aaron D. Little, Campbell, CA (US); Gregory G. Foisy, Tracy, CA (US)

(73) Assignee: Western Digital Technologies, Inc., Irvine, CA (US)

( * ) Notice: Subject to any disclaimer, the term of this patent is extended or adjusted under 35 U.S.C. 154(b) by 788 days.

(21) Appl. No.: 12/026,308

(22) Filed: Feb. 5, 2008

(51) Int. Cl.
*G11B 21/08* (2006.01)
(52) U.S. Cl. .................................... 360/264.2
(58) Field of Classification Search .......... None
See application file for complete search history.

(56) References Cited

U.S. PATENT DOCUMENTS

| | | | |
|---|---|---|---|
| 5,615,068 A * | 3/1997 | Matsuda et al. | 360/264.2 |
| 5,644,452 A | 7/1997 | Cox et al. | |
| 5,818,667 A * | 10/1998 | Larson | 360/264.2 |
| 5,905,609 A | 5/1999 | Butler et al. | |
| 5,909,338 A | 6/1999 | Butler et al. | |
| 5,953,183 A | 9/1999 | Butler et al. | |
| 6,168,459 B1 | 1/2001 | Cox et al. | |
| 6,856,490 B2 * | 2/2005 | Rosner et al. | 360/264.2 |
| 6,970,329 B1 | 11/2005 | Oveyssi et al. | |
| 6,980,391 B1 | 12/2005 | Haro | |
| 7,082,012 B2 * | 7/2006 | Macpherson et al. | 360/97.02 |
| 7,227,725 B1 | 6/2007 | Chang et al. | |
| 7,667,931 B1 * | 2/2010 | Brause et al. | 360/264.2 |
| 2002/0149885 A1 | 10/2002 | Dague et al. | |
| 2005/0013055 A1 | 1/2005 | Ho et al. | |
| 2006/0050429 A1 | 3/2006 | Gunderson et al. | |
| 2006/0276058 A1 * | 12/2006 | Freeman et al. | 439/67 |

* cited by examiner

*Primary Examiner* — Daniell L Negron
*Assistant Examiner* — Tamara Ashford

(57) ABSTRACT

A novel disk drive includes a flex cable having a first end portion fixed to an actuator assembly, a second end portion fixed to a flex cable bracket, and a free portion between the first and second end portions. The free portion joins the second end portion at a flex exit location. The flex cable bracket includes a flex alignment post that protrudes into a corresponding hole in a disk drive base. A distance between the flex exit location and the actuator pivot axis is at least 4 times greater than a distance between the flex exit location and the flex alignment post.

10 Claims, 4 Drawing Sheets

DISK DRIVE WITH FLEX CABLE BRACKET HAVING ALIGNMENT POST BY FLEX EXIT LOCATION

FIELD OF THE INVENTION

The present invention relates generally to disk drives, and in particular to flex cable brackets used in disk drives.

BACKGROUND

Conventional information storage devices typically include one or more heads for reading and writing data from and to a disk. For example, in an optical disk drive, the head will typically include a mirror and objective lens for reflecting and focusing a laser beam on to a surface of the disk. In magnetic recording applications, the head will typically include a transducer having a writer that may be of a longitudinal or perpendicular design, and a read element that may be inductive or magnetoresistive. The heads are typically positioned relative to concentric circular tracks of information on the disk by an actuator assembly to which the heads pertain. The angular position of the actuator assembly is typically controlled by a torque produced by a voice coil motor (VCM). A flex cable assembly will typically carry the signals from/to a printed circuit assembly (PCBA) to/from the heads as the heads write and read information recorded in concentric circular tracks on the disks.

FIG. 1 is an exploded top perspective view of a portion of a conventional disk drive (without any cover shown so that interior parts may be viewed). Now referring to FIG. 1, the flex cable assembly 100 typically includes a flex cable 102 that runs from the actuator to a flex bracket 104. The flex bracket typically includes a connector to electrically couple the flex cable to the PCBA. The flex bracket 104 is typically attached to a base 112 of the disk drive 110. The connector typically passes through the disk drive base 112 and therefore typically must be sealed with the disk drive base 112 to prevent contamination from entering the disk drive 110.

In the conventional disk drive 110 of FIG. 1, the flex bracket 104 is positioned relative to the disk drive base 112 by contact between a connector that protrudes from the underside of flex bracket 104 and a plurality of positioning pads 114 on the sides of an opening 116 through the disk drive base 112 (through which the connector passes). Registration of the flex bracket 104 on the positioning pads 114 ensures that the connector will have adequate alignment with a mating connector on the PCBA.

Posts 118 and 120 may be cast into the disk drive base 112. Although the posts 118 and 120 protrude into hole 106 and slot 108 of the flex bracket 104, respectively, the hole 106 and slot 108 have large enough dimensions so that entry of posts 118 and 120 into hole 106 and slot 108, respectively, does not interfere with the positioning of the flex bracket 104 by the positioning pads 114. The flex cable may include a flex stiffener at one or both ends to help control the exit angle θ of the flex cable 102 from the flex bracket 104 and/or the actuator assembly. However, positioning pads 114 serve to control the relative position of the connector of the flex bracket 104 with the PCBA better than they serve to control the exit angle θ and/or the position where the flex cable 102 exits from the flex bracket 104.

The flex cable is typically longer than the shortest length required to span the distance between the actuator assembly and the flex bracket, because it is not desired for the flex cable to constrain the angular range of motion of the actuator. The excess length in the flex cable forms a curve that allows the actuator assembly to be electrically coupled yet mechanically compliant to the applied torque from the VCM. Still, the flex cable exerts some biasing torque on the actuator, which must be overcome and compensated for by the VCM. To control the motion of the actuator assembly, it is desirable for the flex biasing torque to be small, known, and repeatable. However, excessive part-to-part variation in the position of the flex cable attachment points relative to the other disk drive components can cause excessive variation in the flex biasing torque that is experienced by the actuator. Presently millions of disk drives and other information storage devices are manufactured every year. Accordingly, there is need in the art for flex cable brackets that can more precisely position flex cables within disk drives, practically, in a high-volume manufacturing environment.

SUMMARY

A novel disk drive is disclosed and claimed. The disk drive includes a disk drive base, and a spindle motor attached to the disk drive base. At least one disk is attached to the spindle motor. An actuator assembly is rotably attached to the disk drive base about an actuator pivot axis. The actuator assembly includes at least one read head. A flex cable bracket is attached to the disk drive base. A flex cable has a first end portion fixed to the actuator assembly, a second end portion fixed to the flex cable bracket, and a free portion between the first and second end portions. The free portion joins the second end portion at a flex exit location. The flex cable bracket includes a flex alignment post that protrudes into a corresponding hole in the disk drive base. A distance between the flex exit location and the actuator pivot axis is at least 4 times greater than a distance between the flex exit location and the flex alignment post.

DESCRIPTION OF THE PREFERRED EMBODIMENTS

Figure 1:
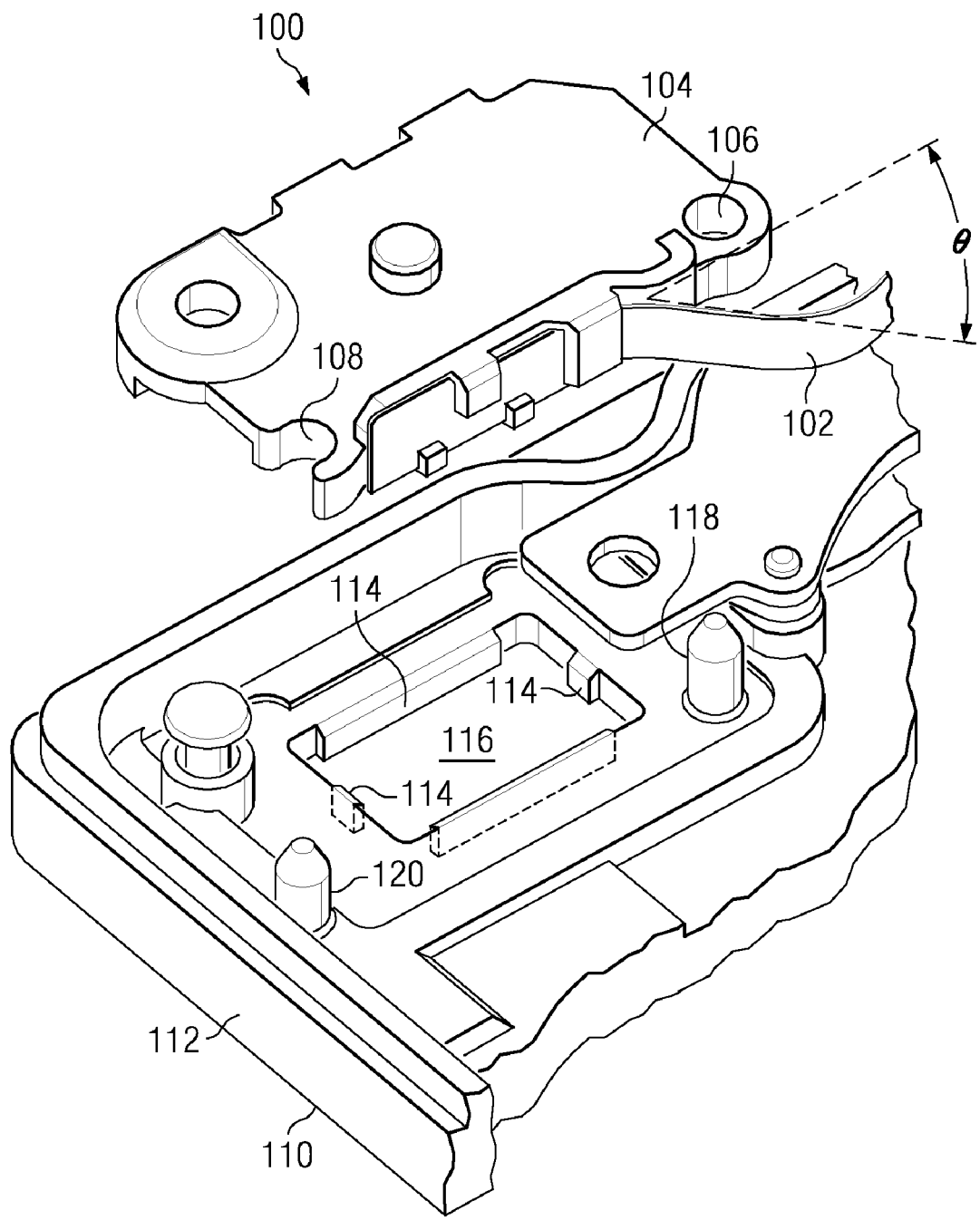
FIG. 1 is an exploded top perspective view of a portion of a conventional disk drive (without any cover shown so that interior parts may be viewed).
Figure 2:
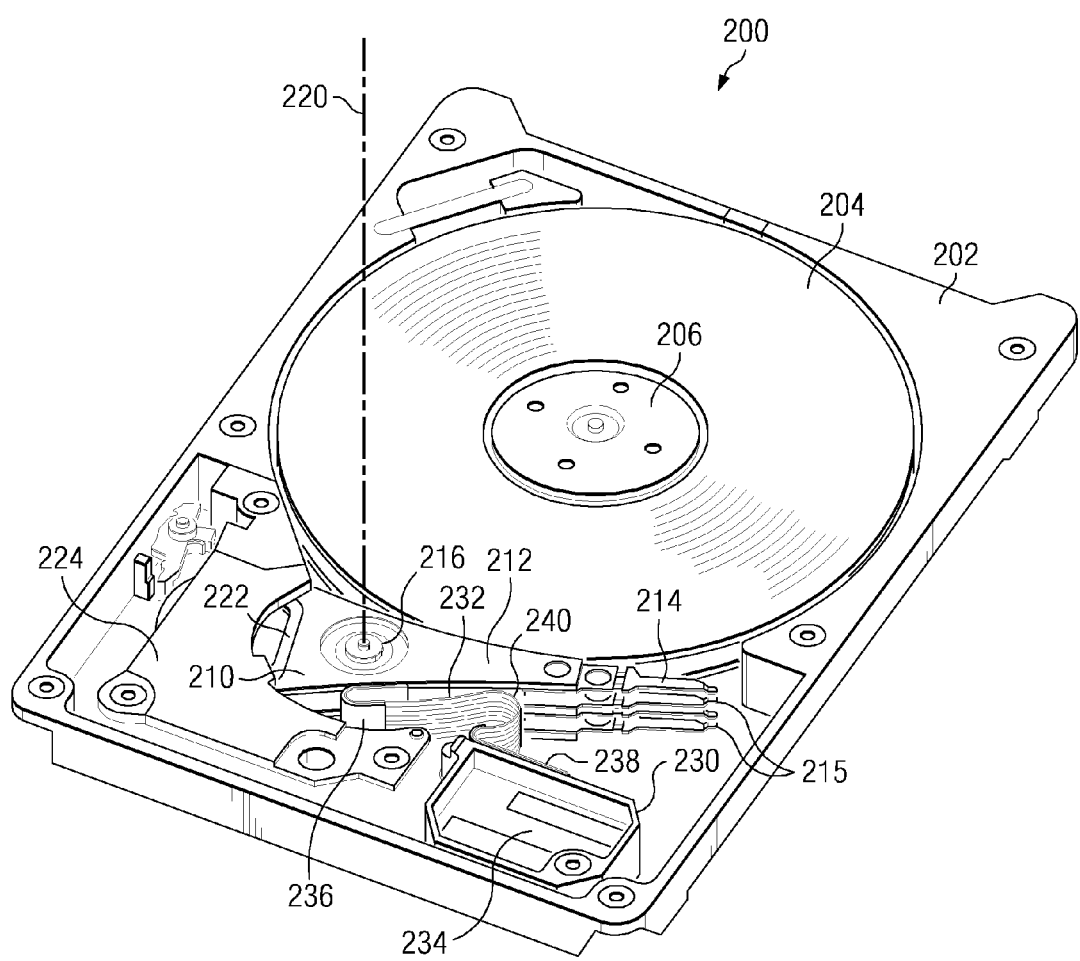
FIG. 2 is a top perspective view of a disk drive according to an embodiment of the present invention (without any cover shown so that interior parts may be viewed).
Figure 3:
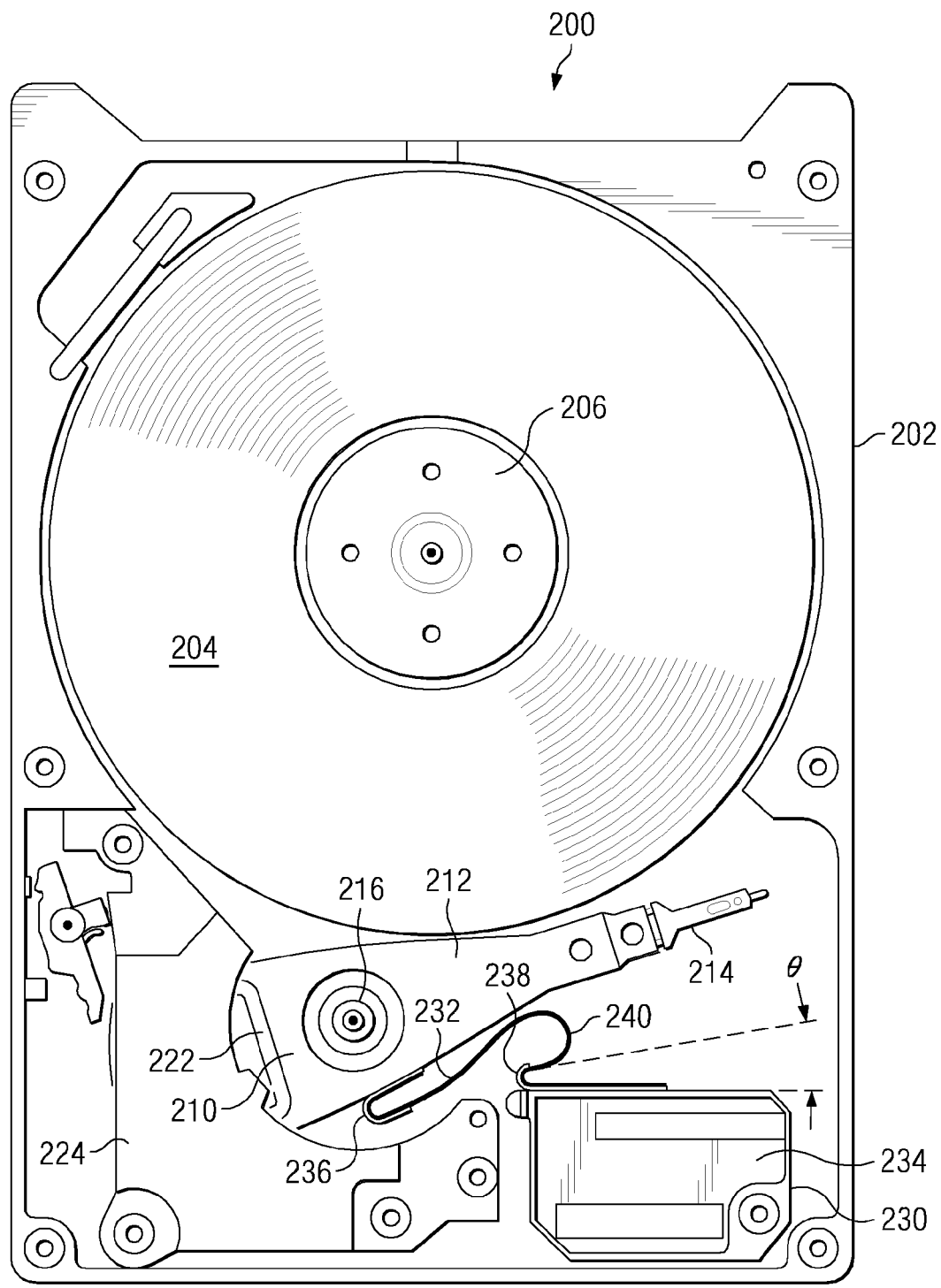
FIG. 3 is a top plan view of the disk drive of FIG. 2.

FIGS. 2 and 3 depict a top perspective view and a top plan view of a disk drive 200 according to an embodiment of the present invention, respectively. The disk drive 200 includes a printed circuit board assembly (PCBA) (mounted to the underside of disk drive 200 and so not readily visible in this view). The disk drive 200 includes a disk drive base 202 and a cover (not shown for ease of illustration of the internal disk drive components). The disk drive base 202 and the cover collectively comprise a housing that encloses disks 204 and several other components. A single disk or multiple disks may be utilized. Each disk 204 includes a media surface on which a plurality of data tracks may be written and/or read by magnetic or optical means. The disk drive 200 further includes a spindle motor 206 for rotating the disks 204. The disk drive 200 further includes an actuator assembly 210 rotatably attached to the disk drive base 202.

The actuator assembly 210 includes actuator arms 212 to which head gimbal assemblies 214 are mounted. It is contemplated that the number of actuator arms and head gimbal assemblies may vary depending upon the number of disks and disk surfaces utilized.

Each head gimbal assembly 214 includes a head 215 with a transducer for at least reading data from a disk surface. The transducer may include both a read element and a writer. In optical and magneto-optical recording applications, the head may also include an objective lens and an active or passive mechanism for controlling the separation of the objective lens from a disk surface of the disk 204. The disk 204 includes opposing disk surfaces which may include one or more magnetic layers. Data may be recorded along data tracks on a single disk surface or both.

The actuator assembly 210 may be rotated about an actuator pivot axis 220 such that each head gimbal assembly 214 is disposed adjacent to various data tracks on the disk 204. To facilitate such rotation (within a limited angular range about actuator pivot axis 220), the actuator assembly 210 includes a pivot bearing cartridge 216.

The actuator assembly 210 of FIGS. 2 and 3 further includes a coil that interacts with a magnetic field to function as a voice coil motor (VCM). In the embodiment of FIGS. 2 and 3, the VCM comprises a coil 222, a VCM top plate 224, and a permanent magnet the view of which is obscured by the VCM top plate 224. The VCM may also include a VCM bottom plate. The coil 222 is positioned adjacent the VCM magnet.

With this configuration, current passing through the coil 222 results in a torque being applied to the actuator assembly 210 for controllably rotating the actuator assembly 210. A change in direction of the current through the coil 222 results in a change in direction of the torque applied to the actuator 210. It is contemplated that other magnet, VCM plate, coil and magnet support configurations may be utilized, such as a multiple coil arrangements, single or double VCM plates and a vertical coil arrangement.

The disk drive 200 of FIGS. 2 and 3 includes a flex cable assembly 230 that carries the current that drives the VCM and carries the signals from/to the PCBA to/from the HGAs 214. The flex cable assembly 230 includes a flex cable 232 that runs from the actuator assembly 210 to a flex bracket 234. The flex bracket 234 includes a connector protruding from its underside, to electrically couple the flex cable 232 to the PCBA. The flex bracket 234 is attached to the disk drive base 202. The connector passes through the disk drive base 202 and therefore is sealed with the disk drive base 202 to prevent contamination from entering the disk drive 200. In the embodiment of FIG. 3, the flex cable 232 includes a first end portion fixed to a flex stiffener 236 to help fix the flex cable 232 to the actuator assembly 210. The flex cable 232 also includes a second end portion fixed to a flex stiffener 238 to help control the exit angle θ of the flex cable 232 from the flex bracket 234. The flex stiffeners 236 and 238 may comprise aluminum, polyimide, and/or stainless steel, among other suitable materials, but if the flex stiffeners 236 and 238 are to include one or more curves as shown in FIGS. 2 and 3, then aluminum or stainless steel may be preferable over polyimide.

In the embodiment of FIGS. 2 and 3, the flex cable 232 is longer than the shortest length required to span the distance between the actuator assembly 210 and the flex bracket 234, because it is not desired for the flex cable 232 to constrain the angular range of motion of the actuator assembly 210. The excess length in the flex cable 232 forms a curved free portion 240 that allows the actuator assembly 210 to be electrically coupled yet mechanically compliant to the applied torque from the VCM. Flex exit angle θ is measured at the flex exit location (where free portion 240 meets the flex stiffener 238).

Figure 4:
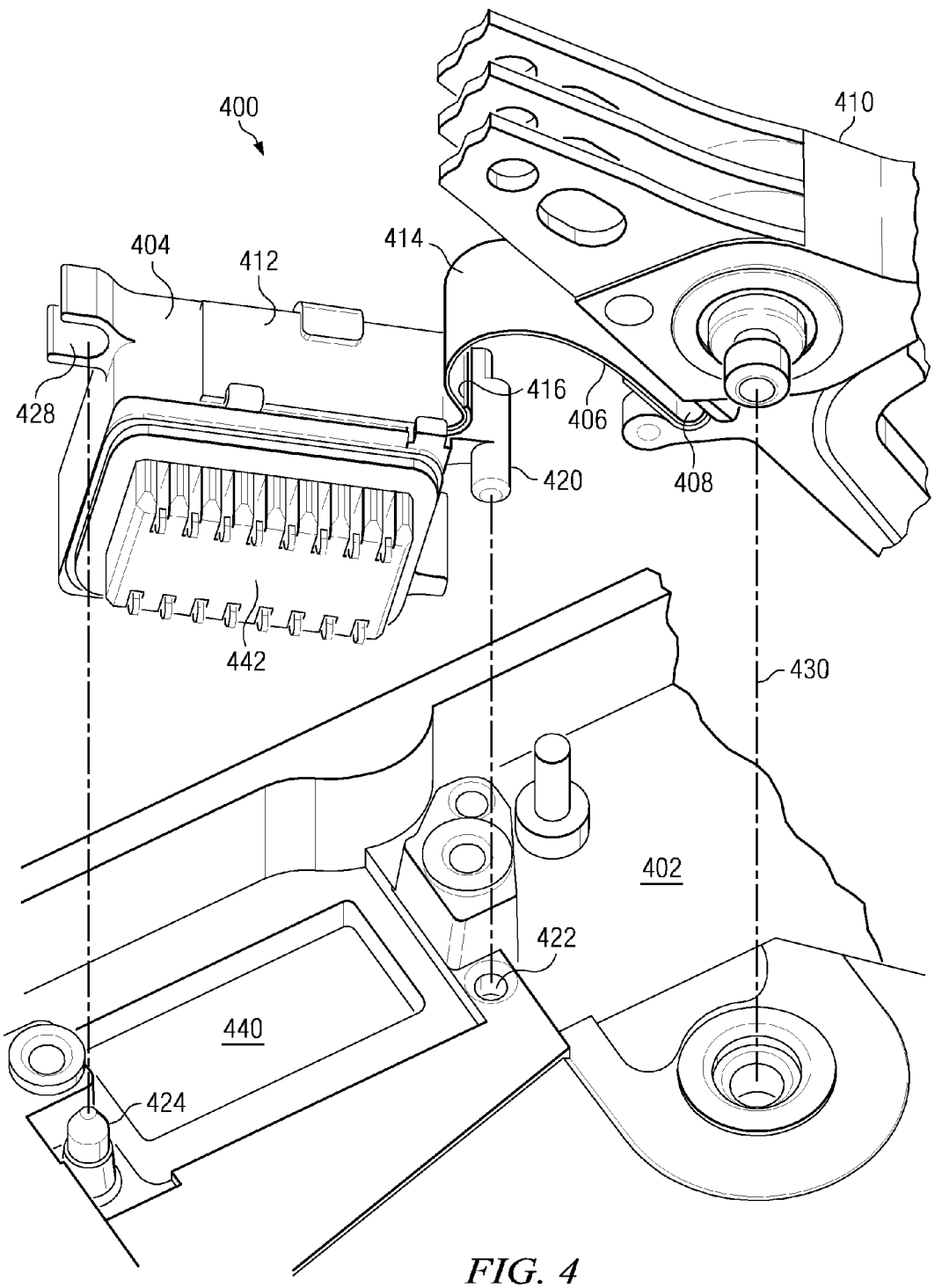
FIG. 4 is an exploded top perspective view of a portion of a disk drive according to an embodiment of the present invention (without any cover shown so that interior parts may be viewed).

FIG. 4 is an exploded top perspective view of a portion of a disk drive according to an embodiment of the present invention (without any cover shown so that interior parts may be viewed). Flex cable assembly 400 includes a flex cable bracket 404 that is attached to the disk drive base 402. For example, the flex cable bracket 404 may comprise nylon, acetal resin plastic, polyetherimide, polycarbonate plastic, and/or liquid crystal polymer. Flex cable 406 has a first end portion 408 fixed to the actuator assembly 410, and a second end portion 412 fixed to the flex cable bracket 404. Flex cable 406 also has a free portion 414 between the first and second end portions 408, 412. The free portion 414 joins the second end portion 412 at a flex exit location 416.

In the embodiment of FIG. 4, the flex cable bracket 404 includes a flex alignment post 420 that protrudes into a corresponding hole 422 in the disk drive base 402. Preferably, the hole 422 is sized so that the flex alignment post 420 has a precision fit with the hole 422, such as a press fit or a slip fit. Also, for example, the hole 422 may be a blind hole rather than being a through-hole. Preferably but not necessarily, the flex cable bracket 404 and the flex alignment post 420 may be a single component having material continuity rather than being an assembly of subcomponents. Also, preferably but not necessarily, the first and second end portions 408, 412 and the free portion 414 of the flex cable 406 are a single component having material continuity rather than being an assembly of subcomponents.

In the embodiment of FIG. 4, the flex cable bracket 404 is positioned by the interface between the flex alignment post 420 and the hole 422, rather than by registration of the connector 442 of the flex cable bracket 404 with an interior surface of the opening 440. When assembled, the distance between the flex exit location 416 and actuator pivot axis 430 is at least 4 times greater than the distance between the flex exit location 416 and the flex alignment post 420. Such physical proximity of the flex alignment post to the flex exit location 416 may enhance control of the flex exit angle θ and/or the position of flex exit location 416, and therefore reduce variation in flex bias torque applied to the actuator assembly.

In the embodiment of FIG. 4, the disk drive base 402 includes a clocking post 424. The disk drive base 402 and the clocking post 424 may be a single component having material continuity (e.g. where the clocking post 424 is machined and/or cast with the disk drive base 402) rather than being an assembly of subcomponents (e.g. where the clocking post 424 is press-fit into a hole in the disk drive base 402). The flex cable bracket 404 includes a registering surface 428 in contact with the clocking post 424.

In the embodiment of FIG. 4, the flex cable bracket 404 is angularly positioned by the interface between the clocking post 424 and the registering surface 428, rather than by registration of the connector 442 of the flex cable bracket 404 with an interior surface of the opening 440. When assembled, the distance between the registering surface 428 and the flex exit location 416 is at least 5 times the distance between the flex exit location 416 and the flex alignment post 420. The physical proximity of the flex alignment post 420 to the flex exit location 416, relative to the distance between the registering surface 428 and the flex exit location 416, may render the flex exit angle less sensitive to the position of the clocking post 424 and/or the location of contact between the registering surface 428 and the clocking post 424. Therefore, less precise manufacturing methods might be practically used to fabricate the clocking post 424 and/or to facilitate mating of the clocking post 424 with the registering surface 428. This may allow a manufacturing cost reduction (e.g. where clocking post 424 may be cast without subsequent machining, and/or where mating with registering surface 428 may be accomplished with looser tolerances).

In the foregoing specification, the invention is described with reference to specific exemplary embodiments, but those skilled in the art will recognize that the invention is not limited to those. It is contemplated that various features and aspects of the invention may be used individually or jointly and possibly in a different environment or application. The specification and drawings are, accordingly, to be regarded as illustrative and exemplary rather than restrictive. "Comprising," "including," and "having," are intended to be open-ended terms.

What is claimed is:

1. A disk drive comprising:
   a disk drive base;
   a spindle motor attached to the disk drive base;
   at least one disk attached to the spindle motor;
   an actuator assembly rotatably attached to the disk drive base about an actuator pivot axis, the actuator assembly including at least one read head;
   a flex cable bracket attached to the disk drive base; and
   a flex cable having a first end portion fixed to the actuator assembly, a second end portion fixed to the flex cable bracket, and a free portion between the first and second end portions, the free portion joining the second end portion at a flex exit location;
   wherein the flex cable bracket includes a flex alignment post that protrudes into a corresponding hole in the disk drive base, and a distance between the flex exit location and the actuator pivot axis is at least 4 times greater than a distance between the flex exit location and the flex alignment post; and
   wherein the disk drive base includes a clocking post, and the flex cable bracket includes a registering surface in contact with the clocking post, the distance between the registering surface and the flex exit location being at least 5 times the distance between the flex exit location and the flex alignment post.

2. The disk drive of claim 1 wherein the flex cable bracket and the flex alignment post are a single component having material continuity rather than being an assembly of subcomponents.

3. The disk drive of claim 1 wherein the corresponding hole is a blind hole rather than being a through-hole.

4. The disk drive of claim 1 wherein first and second end portions and the free portion of the flex cable are a single component having material continuity rather than being an assembly of subcomponents.

5. The disk drive of claim 1 wherein the flex cable bracket includes a flex stiffener subcomponent, and the second end portion is fixed to the flex stiffener subcomponent.

6. The disk drive of claim 2 wherein the flex cable bracket comprises a material selected from the group consisting of nylon, acetal resin plastic, polyetherimide, polycarbonate plastic, and liquid crystal polymer.

7. The disk drive of claim 5 wherein the flex stiffener subcomponent comprises a material selected from the group consisting of aluminum, polyimide, and stainless steel.

8. The disk drive of claim 5 wherein the flex stiffener subcomponent is curved.

9. The disk drive of claim 1 wherein the disk drive base and the clocking post are a single component having material continuity rather than being an assembly of subcomponents.

10. The disk drive of claim 8 wherein the flex stiffener subcomponent comprises a material selected from the group consisting of aluminum and stainless steel.

* * * * *